United States Patent [19]

Matey

[11] Patent Number: 4,584,481

[45] Date of Patent: Apr. 22, 1986

[54] METHOD OF TESTING A PANEL ASSEMBLY OF A COLOR CATHODE-RAY TUBE

[75] Inventor: James R. Matey, Mercerville, N.J.

[73] Assignee: RCA Corporation, Princeton, N.J.

[21] Appl. No.: 671,128

[22] Filed: Nov. 13, 1984

[51] Int. Cl.[4] .................... G01N 21/64; H01J 9/227; H01J 9/42

[52] U.S. Cl. ................ 250/459.1; 250/461.1; 250/486.1; 354/1; 445/63

[58] Field of Search .............. 250/458.1, 459.1, 461.1, 250/491.1, 372, 365, 486.1, 505.1; 354/1; 378/34; 445/63, 47, 52; 430/23, 24

[56] References Cited

U.S. PATENT DOCUMENTS

| | | | |
|---|---|---|---|
| 3,514,208 | 5/1970 | Levin | 445/63 |
| 3,522,432 | 8/1970 | Ortlieb | 250/365 |
| 3,970,456 | 7/1976 | Branton | 354/1 |
| 4,112,562 | 9/1978 | D'Amato | 445/47 |

FOREIGN PATENT DOCUMENTS 33567  3/1978  Japan ........................... 430/34

Primary Examiner—Carolyn E. Fields
Attorney, Agent, or Firm—E. M. Whitacre; D. H. Irlbeck; T. H. Magee

[57] ABSTRACT

A method of testing a panel assembly of a color cathode-ray tube, prior to sealing a faceplate panel of the assembly to a funnel section of the tube, detects defects in the assembly including dents and misregistration of an apertured shadow mask mounted therein adjacent to a luminescent screen disposed on the faceplate panel. The screen is exposed to radiation passed through apertures in the mask including ultraviolet but substantially excluding visible radiation, and examined for variations in color from light emitted by the screen, whereby the variations in color are indicative of defects in the assembly.

10 Claims, 1 Drawing Figure

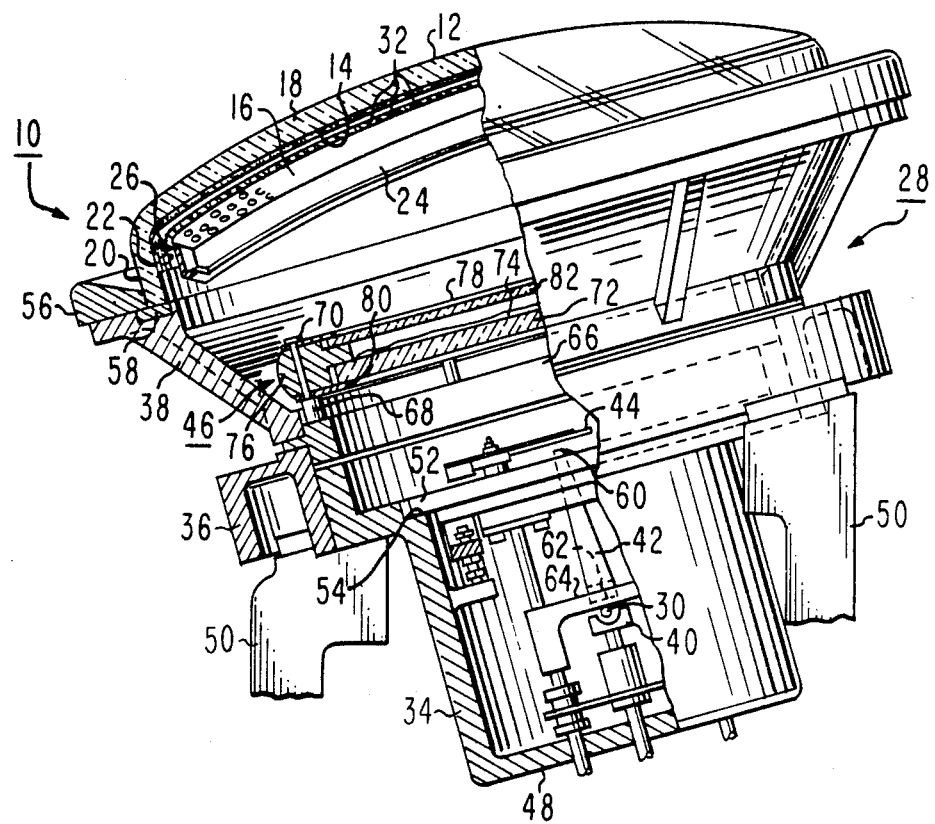

METHOD OF TESTING A PANEL ASSEMBLY OF A COLOR CATHODE-RAY TUBE

BACKGROUND OF THE INVENTION

This invention pertains to a method of testing a panel assembly of a color cathode-ray tube prior to sealing a faceplate panel of the assembly to a funnel section of the tube in order to detect defects in the assembly.

In manufacturing cathode-ray tubes for use in color television, three major components are assembled into the finished color kinescope or cathode-ray tube. These components are the electron gun assembly, the funnel section, and the panel assembly which includes an apertured shadow mask mounted therein adjacent to a luminescent screen of red, green and blue phosphors. Defects in any of these components can cause failure of the finished cathode-ray tube. If the defects are detected before the final assembly, the cost of scrapping the component is relatively low. However, if the defects are detected at final inspection of the tube, the cost of scrapping the finished product is significantly higher.

Due to process and material variations, shadow masks are not interchangeable. Hence, early during the fabrication of the panel assembly, each shadow mask is uniquely paired to a particular faceplate panel, so that the mask and panel then go through subsequent fabrication steps together and are assembled together in the final product. Phosphor slurries and a black matrix application are deposited on the inner surface of the panel in chemical photoresist processes which utilize the shadow mask as a photolithographic mask during light exposure steps. The light exposure steps are carried out on a photoexposure apparatus known in the art as a "lighthouse".

The lighthouse is designed to expose the photosensitive films by projecting light from a small area radiation source through the shadow mask. Beams of light pass through the apertures of the shadow mask to form a pattern, substantially of the same shape as the apertures in the mask, on the photosensitive films. The lighthouse is designed so that these beams of light follow the same trajectories through the shadow mask as will the electron beams in the finished product. Since the color cathode-ray tube uses 3 electron guns (one for each of the three colors red, green and blue), the lighthouse will generally have some provision for adjusting the position of the light source and adjusting the optics of the lighthouse to mimic the effect of the three different electron guns. When the lighthouse is adjusted to its "red" position, the light beams projected through the shadow mask will fall on that part of the phosphor screen upon which the electron beam from the red electron gun will fall in the finished product. Similarly, when the lighthouse is adjusted to its "blue" and "green" positions, the light beams will fall on those parts of the phosphor screen upon which electrons from the blue and green guns will fall. Hence, in a succession of photolithographic steps, the lighthouse can be used to selectively deposit red, green, and blue phosphors at the positions on the phosphor screen upon which electrons from the red, green, and blue electron guns will fall, respectively. The lighthouse may also be used to deposit a black matrix in the regions where the electron beams will not fall.

In each of these photolithographic steps, the shadow mask must be installed in its panel for the lighthouse exposure and then removed temporarily for chemical processing of the photoresist. This handling often results in dents which destroy the correspondence between the mask and the phosphor or matrix patterns laid down in previous steps. With the correspondence destroyed, the electron beams in the final product will no longer land on the intended phosphor sites. For example, electrons from the blue gun might land on red phosphors. In such a case, the tube will not reproduce colors correctly. In general, any distortion of or shift relative to the panel of the shadow mask will lead to similar problems. In addition, the faceplate panel itself may have screening defects therein, such as the contamination of one color phosphor with another, incomplete filling by phosphor or matrix, and scratches on the screen. At the present time, many of the aforementioned defects only become apparent after the electron gun assembly, funnel section and panel assembly are sealed together, and the cathode-ray tube is tested for color purity. The present invention provides a novel method of effectively testing the panel assembly for the aforementioned defects prior to the final step of frit sealing the faceplate panel to the funnel section of the tube.

SUMMARY OF THE INVENTION

The present invention comprises a method of testing a panel assembly of a color cathode-ray tube, prior to sealing a faceplate panel of the assembly to a funnel section of the tube, in order to detect defects in the assembly including dents and misregistration of an apertured shadow mask mounted therein adjacent to a luminescent screen disposed on the faceplate panel. The screen is exposed to radiation passed through apertures in the mask including ultraviolet but substantially excluding visible radiation. The paths of the beams of this radiation are chosen to follow the trajectories through the shadow mask which the electrons of one of the electron guns of the final product should follow. The ultraviolet radiation causes the screen to fluoresce, and the screen is then examined for variations in color. If the correspondence between the panel and the shadow mask has not been altered and if the phosphors have been correctly placed on the panel, the screen will fluoresce with a uniform color over its entire area, the color corresponding to the electron gun which is being mimicked by the ultraviolet radiation. Defects in the panel, which would lead to color purity problems in the final product, will be revealed as a nonuniformity in the color of the screen.

BRIEF DESCRIPTION OF THE DRAWING

The FIGURE of the drawing is a partial cross-sectional elevation view of a lighthouse apparatus utilized for performing the present novel method.

DETAILED DESCRIPTION OF THE PREFERRED EMBODIMENT

In the FIGURE of the drawing, there is shown a panel assembly 10 comprising a faceplate panel 12, a luminescent screen 14 disposed on the inner surface of the panel 12, and an apertured shadow mask 16 mounted in the panel 12 at a position near and spaced from the luminescent screen 14. The faceplate panel 12 includes a viewing window 18 and a sidewall 20. A plurality of mounting studs 22 extend inwardly from an inner surface of the sidewall 20 for use in mounting the shadow mask 16 to the panel 12. The shadow mask 16 is attached along the margins thereof to a mask frame 24 which has mounting means 26 attached thereto, the extended ends of which are adapted to fit on the studs 22 in a predetermined relationship. The luminescent screen 14 may comprise a pattern of red, green and blue phosphor stripes resulting from a screening process involving the selective exposure and processing of photosensitive films containing colored phosphor slurries. The panel assembly 10 is shown positioned on a photo-exposure apparatus known in the art as a "lighthouse" 28. The lighthouse 28 is designed to expose the photosensitive films by projecting light (which includes both ultraviolet and visible radiation) from a small area radiation source 30 incident on the shadow mask 16, permitting beams of light to pass through apertures 32 in the mask 16 to form a pattern, substantially of the same shape as the apertures 32 in the mask 16, on the photosensitive films.

A typical lighthouse 28 comprises a housing 34 which includes a base 36, a panel support 38, the radiation source 30, a reflector 40, a collimator 42, an eclipser 44, and a lens package 46. The housing 34 is a cylindrical cup-shaped casting, closed at one end by an integral end wall 48, which is supported at the desired angle by legs 50 upon which the base 36 of the housing 34 rests. The other end of the housing 34 is closed by a plate 52 which fits in a circular recess 54 in the housing 34. The plate 52 has a central hole therein through which the collimator 42 extends. The panel support 38 is adapted to support the faceplate panel 12 in accurate alignment over the radiation source 30, as shown in the FIGURE. The exact position of the faceplate panel 12 with respect to X and Y coordinates (X and Y being orthogonal axes perpendicular to the central longitudinal axis of the lighthouse 28) is determined by three locating stops 56 (one shown) which are attached to the panel support 38, and by associated pads 58 which contact a seal edge of the panel 12 and locate the panel 12 along a Z direction (along the central longitudinal axis of the lighthouse). In the embodiment shown, the panel 12 is held against the stops 56 and pads 58 by the force of gravity since the entire lighthouse 28 is tilted with respect to the vertical direction.

The collimator 42 comprises a light pipe in the form of a tapered quartz rod with the narrow end 60 extending slightly above the plate 52 and constituting a small area point or line source of radiation for the lighthouse 28. The wider end 62 of the collimator 42 is held in position by a bracket 64 opposite the radiation source 30. The eclipser 44 normally blocks the upward path of the radiation emitted from the narrow end 60 of the collimator 42, but is operated to swing out from the radiation path when it is desired to expose the photosensitive films to the radiation. The collimator 42, eclipser 44 and lens package 46 are positioned in alignment between the radiation source 30 and the faceplate assembly 10. The reflector 40 is positioned below the radiation source 30 which, in the present embodiment, comprises a mercury vapor lamp.

The lens package 46 is mounted on a lens support ring 66 and standoff spacers 68 with bolts 70. The lens package 46 of a typical lighthouse 28 normally includes a correction lens 72 having a light-intensity correcting filter 74 on the upper surface thereof and a trimmer lens, which are held and spaced from each other by a separator ring 76, an upper clamp 78 and a lower clamp 80. However, in accordance with the novel invention, the present trimmer lens, designed to mimic the "green" electron gun, has been replaced with an ultraviolet (UV) transmitting, visible absorbing filter 82 in order to filter out the visible radiation from the radiation source 30. The UV transmitting filter 82 comprises a dark glass filter, nearly black, which transmits UV radiation but absorbs visible radiation, and is chosen to have optical characteristics similar to the trimmer lens so as not to change the radiation path. Such a filter 82 is available as the U-330 filter from Hoya Optics Inc., Fremont, Calif.

In performing the present testing method, the faceplate panel 12, having the completed luminescent screen 14 on the inner surface thereof and the apertured shadow mask 16 mounted therein, is placed in position on the panel support 38 of the modified lighthouse 28, as shown in the FIGURE. The lighthouse 28 operation is then initiated by swinging the eclipser 44 out of the radiation path, thereby permitting radiation from the source 30 to pass upward through the lens package 46. The UV transmitting, visible absorbing filter 82 does not allow the visible light to pass therethrough, thus exposing the apertures 16 and luminescent screen 14 to ultraviolet but not visible light. The ultraviolet light excites the phosphors incident thereto, thereby resulting in a fluorescence which is visible to the human eye. The luminescent screen 14 is then examined for variations in color which are indicative of defects in the panel assembly 10. This examining step could be performed manually by an operator viewing the luminescent screen 14, automatically by an appropriate color-selective photometer, or a combination thereof. If done manually by an operator, it is preferred that the viewing step be performed in an enclosure with a relatively low ambient light level in order to facilitate the operator's observance of the variations in color. For the same reason, it may also be desirable to block any scattered radiation, emanating from the source 30 within the lighthouse 28 and bypassing the filter 82, from reaching the panel assembly 10 by surrounding the lens package 46 with a strip of opaque material (not shown).

The essence of the present invention is the use of filtered UV light. Heretofore, the visible white light emanating from the mercury vapor lamp would wash out the fluorescence of the phosphors, thereby swamping the variations in color attributable to defects in the panel assembly 10. Hence, an operator would only see intensity variations. However, the intensity variations due to defects are obscured by other intensity variations which are not related to defects, making it very difficult for the operator to spot defects. In other words, if the light is not filtered, dents in the shadow mask 16 appear as variations in intensity of an essentially white field, which has other intensity variations that are not related to dents and will probably not result in defects in the cathode-ray tube. Such other intensity variations are due in part to filming and aluminization non-uniformities.

Using the present novel method, an operator can spot defects very easily since they appear as color variations on a field of otherwise uniform color. Shadow mask 16 dents appear as variations in color, and the observer simply examines the viewing window 18 of the faceplate panel 12 for color contrast. The defects are particularly noticeable when the path of the radiation is moved with respect to the panel assembly 10, thereby causing the background field to change color, from green to red for example, while the defect features also change color, such as from red to blue. Such a moving step may be performed by dithering the apparent position of the radiation source 30. In the present embodiment, dithering or jiggling the position of the light source 30 representing the "green" electron gun, while monitoring the green light-intensity level at several points on the faceplate panel 12, would provide a measure of shadow mask 16 misregistration. It has also been discovered that the present testing method can be performed effectively even after the step of aluminizing the luminescent screen 14 wherein a nominally nontransparent (to visible or UV light) aluminum layer, having a thickness of about 0.3 micrometer, is deposited on the inside surface of the screen 14. Pinholes in the aluminum layer, resulting from current processing techniques, permit enough radiation to pass therethrough and, thereby, produce a visible fluorescence of the phosphors in the screen 14.

Before installation of the present testing method, certain safety measures should be considered. It is likely that the filtered light from the modified lighthouse 28 would be more dangerous to a human eye than unfiltered light, since the brightness of the unfiltered light forces the iris of the eye to close, while the filtered light, particularly in a low ambient, will be going into an eye with the iris wide open. This is not a serious problem since UV-stop goggles and masks are available for wear by an operator. In addition, a safety switch may be installed on the lighthouse 28 which will close the eclipser 44 any time there is not a panel assembly 10 in place on the lighthouse 28.

The present method provides a quick and reliable factory test for detecting defects in the panel assembly 10 including both dents and misregistration of a shadow mask 16 mounted therein. By testing the panel assembly 10 before frit sealing the faceplate panel 12 to the funnel section of the tube, a highly significant savings from factory scrap reduction is able to be achieved, particulary in the 25 V and larger panel assemblies where dents are a more severe problem.

What is claimed is:

1. A method of testing a panel assembly of a color cathode-ray tube prior to sealing a faceplate panel of said assembly to a funnel section of said tube in order to detect defects in the assembly including dents and misregistration of an apertured shadow mask mounted therein adjacent to a luminescent screen disposed on said faceplate panel comprising the steps of:

exposing said screen to radiation passed through apertures in said mask including ultraviolet but substantially excluding visible radiation, and examining said luminescent screen for variations in color from light emitted by the screen, whereby said variations in color are indicative of defects in said assembly.

2. A method as recited in claim 1 wherein said exposing step is performed by positioning said panel assembly on a lighthouse having a radiation source therein emanating both visible and ultraviolet radiation, and filtering out the visible radiation from said radiation source.

3. A method as recited in claim 2 wherein said filtering step is performed by passing said radiation through an ultraviolet transmitting, visible absorbing filter.

4. A method as recited in claim 3 wherein said passing step is performed by installing said ultraviolet transmitting, visible absorbing filter into a lens package of said lighthouse in place of a trimmer lens therein.

5. A method as recited in claim 3 wherein said ratiation source comprises a mercury vapor lamp, and wherein said luminescent screen comprises a pattern of red, green and blue phosphors.

6. A method as recited in claim 3 further comprising the step of moving the path of said radiation with respect to said panel assembly in order to detect any misregistration of said mask.

7. A method as recited in claim 6 wherein said moving step is performed by dithering the apparent position of said radiation source while monitoring the light-intensity level at several locations on said faceplate panel.

8. A method as recited in claim 3 wherein said examining step is performed manually by an operator viewing said luminescent screen.

9. A method as recited in claim 8 wherein said viewing step is performed in an enclosure with a relatively low ambient light level.

10. A method as recited in claim 9 further comprising the step of blocking scattered radiation, emanating from said radiation source within said lighthouse and bypassing said filter, from reaching said panel assembly.

* * * * *